Dec. 11, 1956 A. V. PIKE Plant Pat. 1,536
HYBRID BUDDLEIA PLANT
Filed July 13, 1955
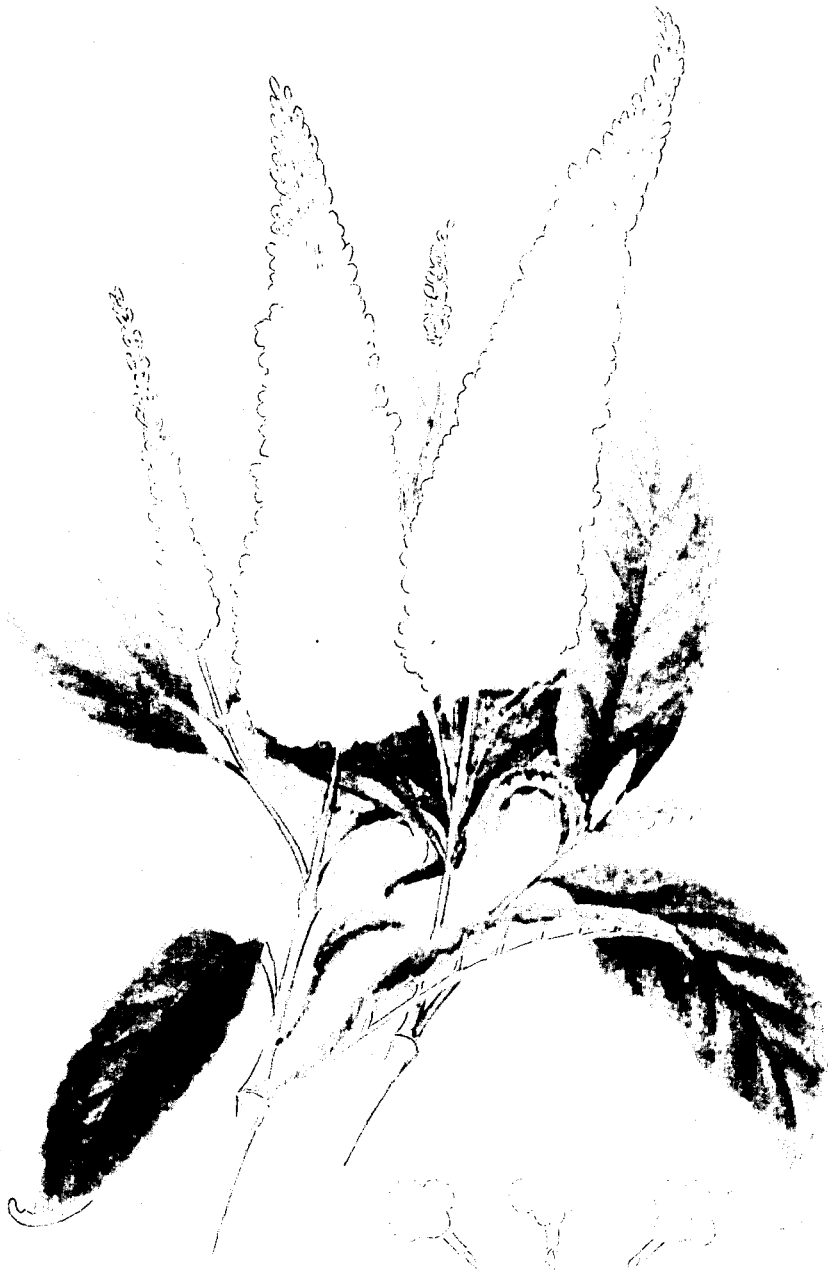
WITNESS
Addison E. Avery
INVENTOR
Albert V. Pike,
by: John A. Leonard,
his ATTY.

United States Patent Office

Plant Pat. 1,536

Patented Dec. 11, 1956

1,536

HYBRID BUDDLEIA PLANT

Albert Victor Pike, Chiddingstone, Kent, England, assignor to John J. Grullemans, Cleveland, Ohio Application July 13, 1955, Serial No. 521,942

1 Claim. (Cl. 47—60)

This invention relates to a new and distinct hybrid species of Buddleia plant.

The present Buddleia plant was developed by the intentional crossing of a Buddleia Madagascariensis plant, as the seed or pistillate parent, with Buddleia Asiatica plant, as the pollen or staminate plant, the former being a native of Madagascar and the latter a native of India. Neither of the parents is patented. The present plant is a selected one of the seedlings of the crossing.

The new plant was first asexually reproduced at Hever Castle Gardens, Chiddingstone, Kent, England, by means of cuttings of half-ripened wood, as follows:

Cuttings of half-ripened lateral shoots, which are side growths of young wood which are just beginning to become firm at the base, were taken off the parent with a heel of the older wood and then inserted into sandy compost in a propagating case. These cuttings were kept in a moist, confined atmosphere, and shaded from intense sunlight, until rooting took place. After rooting took place, ventilation was admitted to the case and the rooted plants were potted off separately to form separate individuals.

THE DRAWING

In the drawing, the large central figure is a reduced scale illustration of terminal portions of a branch of the plant with some terminal inflorescences in bloom thereon, and the three small illustrations therebeneath are full scale perspective views of florets of the plant, taken at different locations along one of the spikes and showing the differences in color at the different locations, the floret at the left being a newly opened one from near the upper end of the spike, the floret in the center being one from the central portion of the spike, and the floret at the right being one from the lower portion of the spike.

THE ROOT OF THE PLANT

The plant varies from shallow rooted to medium deep rooted.

The main roots are of average size for Buddleia plants and are somewhat coarse with some fibrous lateral roots.

THE EXPOSED PLANT STRUCTURE

The plant is a bushy shrub and is rather suffrutescent. In growth it is chiefly upright though somewhat spreading, open, and loose. The top varies in shape from irregular to rounded.

The plant grows to a height of about ten feet and to about the same distance through, this feature being very unusual for any Buddleia plant except the Buddleia Madagascariensis, seed parent of the present plant. The exposed part of the plant as a whole is wide and somewhat irregular.

The plant is very vigorous in growth. It has better drought resistance than most trees and shrubs. It appears to be free from attacks by insect pests and the known diseases which usually attack Buddleia plants.

The plant prefers moderate sun, preferably with some temporary shade from the hottest sun. It prefers also a south or southwest exposure and well drained semi-rich alkaline soil.

THE PARTS OF THE EXPOSED PLANT

*The main stalks and branches*

The main stalks grow generally upright but semi-drooping. They are very much branched and are relatively stiff and tough so that they support the foliage and bloom amply. They grow to a length of ten feet.

The new growth is a woolly grey or a green masked with a woolly covering, comparable to Maerz & Paul Plate 17–A–2, the old growth being similar in color but less woolly, and striated with shaggy bark. The main stalk grows singly from the roots.

The branches of the main stalks are oppositely arranged. They have a downy surface texture and are produced abundantly. They are relatively stiff and tough and adequate to support the bloom and foliage. Generally they are quite long and semi-arching.

FOLIAGE

The foliage is generally dense, the leaves ranging from abundant to average.

The leaves, on their upper faces, are green, ranging from a Peridot green comparable to Maerz & Paul Plate 22–L–6 to a green comparable to Maerz & Paul Plate 23–L–7. They are grey and woolly on the bottom, comparable to Maerz & Paul Plates 17–A–2 and 20–A–1.

The old leaves are not quite as woolly on the bottom as the new. The color of both the old and new leaves is generally uniform.

The leaves are rather large, averaging about six inches in length but ranging from about three inches up to ten inches in length and from one inch to two and one-half inches in width. They are of the usual shape for Buddleia leaves, being somewhat ovate and oblong and having serrated margins. They are tapering at the base and acuminate at the apex. They are relatively thick with smooth and somewhat glaucous upper faces. The lower faces are rough because of venation.

Their persistency on the plant is excellent. The leaf stems are of a greyish-white averaging about three-quarters of an inch in length. They have a wooly surface texture and are relatively strong.

THE BLOOM

The plant produces the best blooms when grown in moderate sunshine with partial shade from the hottest sun, in a southern and western exposure, in dry seasons, and in well drained but moist semi-alkaline soil of a loam or sandy loam type. The plant blooms continuously for about three months of the year.

The buds are small with a pubescent aspect. They are of a pale primrose when the petals begin to unfurl changing to a buff when half blown.

The calyxes or bud coverings are four cleft at the apex, oval and somewhat pyriform. They are relatively small, being about one-eighth of an inch long. They are lanate and somewhat pubescent.

The peduncles of the flower average from ten to fifteen inches and are somewhat pubescent. They are greyish-white and strong.

The pedicels or stalks of the individual florets are from one eighth of an inch to one-sixth of an inch in length. They have a pubescent surface and are greyish-white in color.

The florets open more rapidly the higher the temperature. The individual florets average about three-eighths of an inch in diameter. They are borne in tens of thousands on each plant.

The inflorescences as a whole are borne in truss-like cymes of which each cyme is composed of spikes. Each spike is composed of a tremendous quantity of florets. The individual inflorescences of the plant last from five to eight days when uncut and from four to six days when cut.

The florets have the usual four petals and cruciform shape. When the florets first open they are a very light or whitish yellow comparable to Maerz & Paul Plate 9–H–1. They change later to a sunflower or dandelion yellow, comparable to Maerz & Paul Plate 9–L–4, and finally to cavalry or deep chrome comparable to Maerz & Paul Plate 9–L–7. After four to five days, depending on temperature, the florets gradually begin to fade and change to a brown. The petals are smooth and glistening. The florets of the present Buddleia are larger in diameter than those of any other Buddleia except the Buddleia Colvilli which has the largest diameter florets of any known Buddleia. The florets are not the second longest, however.

The flower has a very strong fragrance of superb quality which lasts well on the cut flowers as well as on the growing flowers.

The stamens are usual in color and quantity with very short creamy white filaments. The pollen is a greyish-white. The styles are about three-sixteenths of an inch long and green in color. The stigmas are about one-sixteenth of an inch long and are green and viscid. Ovaries are present in medium quantity.

So far as is known there are no other Buddleia plants of the same species, this being a hybrid of two known species. It is much more vigorous than either of its parents. It has very much larger flowering cymes than other cultivated Buddleias. It is unique, also, in that its flowers show the colors of its parents and pass through the same color transition from the time when they first open until they fade and brown.

I claim:

The new and distinct hybrid species of Buddleia plant herein shown and described.

No references cited.